| United States Patent [19] | [11] | 4,122,283 |
|---|---|---|
| Yankee | [45] | Oct. 24, 1978 |

[54] 11-DEOXY-CIS-13-PGF$_2$ ANALOGS

[75] Inventor: Ernest W. Yankee, Portage, Mich.

[73] Assignee: The Upjohn Company, Kalamazoo, Mich.

[21] Appl. No.: 774,182

[22] Filed: Mar. 3, 1977

Related U.S. Application Data

[62] Division of Ser. No. 595,869, Jul. 14, 1975, Pat. No. 4,026,909.

[51] Int. Cl.$^2$ .................................................. C07C 177/00
[52] U.S. Cl. ................................... 560/121; 260/410; 260/410.5; 260/410.9 R; 260/413; 562/503
[58] Field of Search ............. 260/468 D, 514 D, 410, 260/410.5, 410.9 R, 413; 560/121

[56] References Cited

U.S. PATENT DOCUMENTS

| 3,873,607 | 3/1975 | Bernady et al. ............... 260/514 |
| 3,914,282 | 10/1975 | Pike ............................... 260/468 |
| 3,932,463 | 1/1976 | Schaus et al. ................. 260/340.7 |
| 3,933,889 | 1/1976 | Magerlin ........................ 260/468 |
| 3,933,899 | 1/1976 | Nelson ........................... 260/473 |
| 3,959,346 | 5/1976 | Schneider ...................... 260/468 |
| 3,962,293 | 6/1976 | Magerlin ........................ 260/408 |

OTHER PUBLICATIONS

Burger, Medicinal Chemistry, p. 81.2, (1960).

*Primary Examiner*—Robert Gerstl
*Attorney, Agent, or Firm*—Robert A. Armitage

[57] ABSTRACT

This invention comprises certain analogs of the prostaglandins in which the double bond between C-13 and C-14 is of the cis configuration. Also provided in this invention, are novel chemical processes and novel chemical intermediates useful in the preparation of the above prostaglandin analogs. These prostaglandin analogs exhibit prostaglandin-like activity, and are accordingly useful for the same pharmacological purposes as the prostaglandins. Among these purposes are blood pressure lowering, labor induction at term, reproductive-cycle regulation, gastric antisecretory action, and the like.

7 Claims, No Drawings

11-DEOXY-CIS-13-PGF$_2$ ANALOGS

The present application is a divisional application of Ser. No. 595,869, filed July 14, 1975, now issued as U.S. Pat. No. 4,026,909 on May 31, 1977.

The present invention relates to prostaglandin analogs for which the essential material constituting a disclosure therefor is incorporated by reference here from U.S. Pat. No. 4,026,909, issued May 31, 1977.

I claim:

1. A compound of the formula

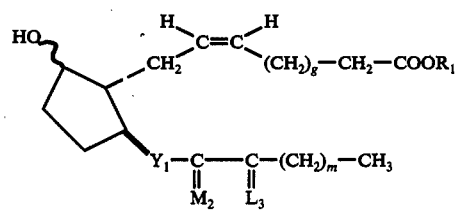

wherein Y$_1$ is cis—CH=CH—; wherein $g$ is 2, 3, or 4; wherein M$_2$ is

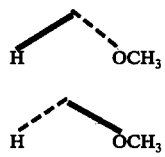

wherein L$_3$ is

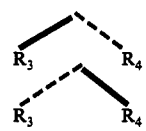

or a mixture of

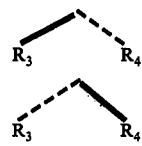

and wherein R$_3$ and R$_4$ are hydrogen or methyl, being the same or different;

wherein $m$ is one to 5, inclusive; and wherein R$_1$ is hydrogen, alkyl of one to 12 carbon atoms, inclusive, cycloalkyl of 3 to 10 carbon atoms, inclusive, aralkyl of 7 to 12 carbon atoms, inclusive, phenyl, phenyl substituted with one, two, or three chloro or alkyl of one to 3 carbon atoms, inclusive, or a pharmacologically acceptable cation.

2. A compound according to claim 1, wherein $g$ is 2.
3. A compound according to claim 2, wherein $m$ is 3.
4. A compound according to claim 3, wherein at least one of R$_3$ and R$_4$ is methyl.
5. A compound according to claim 3, wherein R$_3$ and R$_4$ are both methyl.
6. A compound according to claim 3, wherein R$_3$ and R$_4$ are hydrogen.
7. 15-epi-11-deoxy-cis-13-PGF$_2$α, methyl ester, 15-methyl ether, a compound according to claim 6.

* * * * *